United States Patent [19]

Heitmeier et al.

[11] Patent Number: 4,735,727
[45] Date of Patent: Apr. 5, 1988

[54] DIALYSIS EQUIPMENT

[75] Inventors: Rolf Heitmeier, Kassel; Dieter Rath, Melsungen, both of Fed. Rep. of Germany

[73] Assignee: Intermedicat GmbH, Emmenbrucke, Switzerland

[21] Appl. No.: 844,238

[22] Filed: Mar. 25, 1986

Related U.S. Application Data

[63] Continuation of Ser. No. 460,033, Jan. 21, 1983, abandoned.

[30] Foreign Application Priority Data

Jan. 29, 1982 [DE] Fed. Rep. of Germany ....... 3202831

[51] Int. Cl.$^4$ .............................................. B01D 13/00
[52] U.S. Cl. ...................................... 210/646; 210/87; 210/929
[58] Field of Search ................... 210/929, 87, 646, 90, 210/321.3

[56] References Cited

U.S. PATENT DOCUMENTS

| | | | |
|---|---|---|---|
| 3,979,284 | 9/1976 | Granger et al. | 210/929 X |
| 4,021,341 | 5/1977 | Cosentino et al. | 210/321.3 X |
| 4,381,999 | 5/1983 | Boucher et al. | 210/647 X |

Primary Examiner—Frank Spear
Attorney, Agent, or Firm—Kenyon & Kenyon

[57] ABSTRACT

The dialysis equipment has a dialysate path connectable to a dialysate source 1, and contains a feed pump 6, a dialyzer 10, and a controlled suction pump 13. During the operative phase, this dialysate path is traversed by the dialysate with a constant negative pressure being maintained in the dialysate chamber 101 of the dialyzer 10 relative to the blood chamber 102. In a subsequent measuring phase, the dialysate path is cut off from the dialysate source 1 and from a drain 15 via a valve device 2, 14. The same negative pressure is maintained in the dialysate chamber 101 as in the operative phase. The ultrafiltrate passing from the blood chamber 102 into the dialysate chamber 101 during the measuring phase causes the filling of a volume measuring device 5.

6 Claims, 1 Drawing Sheet

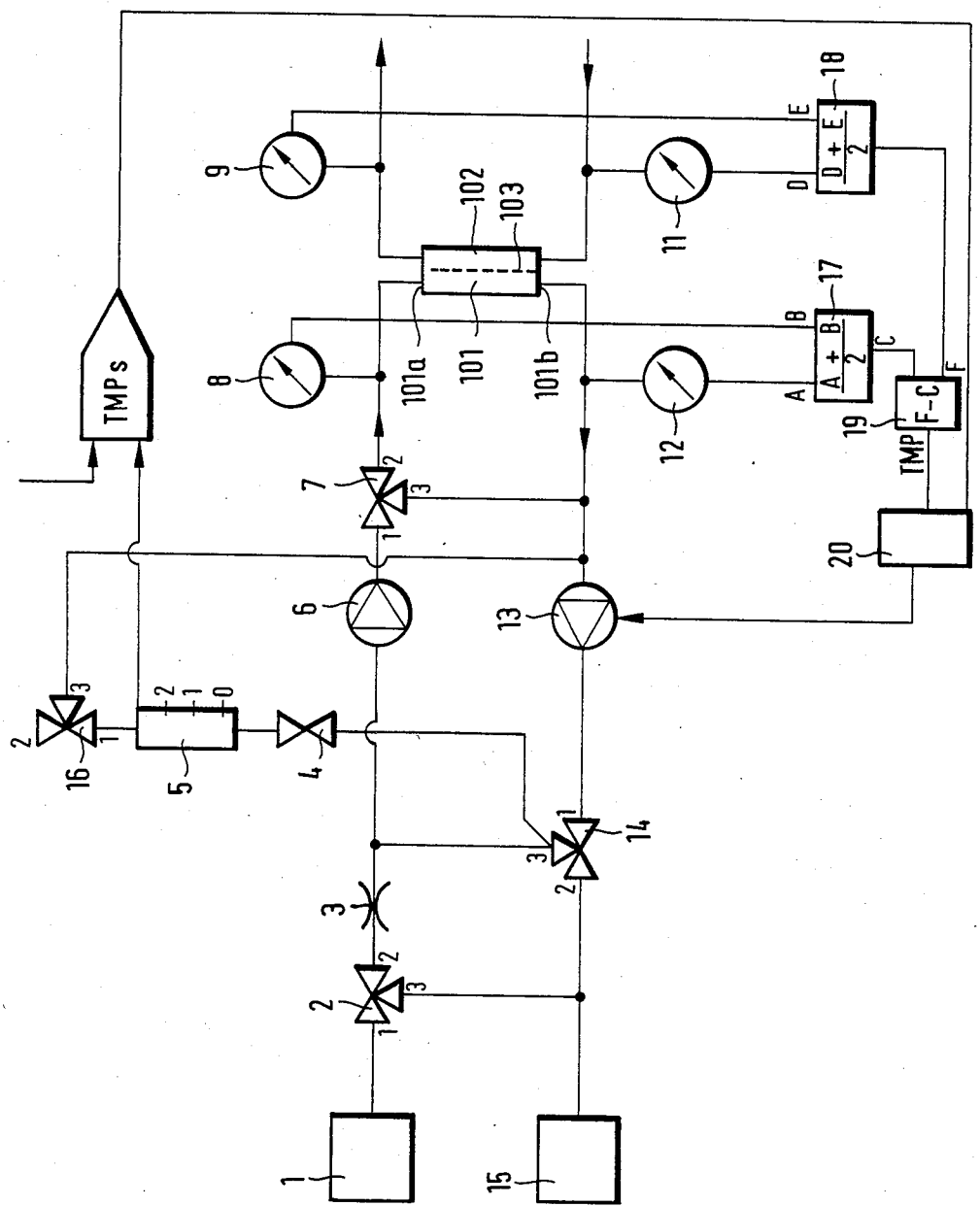

DIALYSIS EQUIPMENT this application is a continuation of application Ser. No. 460,033, filed Jan. 21, 1983, now abandoned.

FIELD OF INVENTION

This invention relates to dialysis equipment and a method for operating same. More particularly, this invention relates to a dialysis system comprising a dialyzer having two chambers separated by a membrane wherein one chamber is connected in a dialysate path and the other chamber is connected in a blood path, a suction pump is disposed in the dialysate path and regulated as a function of the transmembrane pressure, a valve device is provided for disconnecting the dialysate path from a dialysate solution source, and a volume measuring device is connected via a valve to the dialysate path for measuring the liquid overflow volume when the dialysate source is disconnected from the dialysate path.

BACKGROUND OF THE INVENTION

It is the function of dialysis equipment to detoxicate the blood of uremic patients through a semipermeable membrane. A dialyzing fluid is passed through one chamber of the dialyzer and the blood to be detoxicated is passed through another chamber along the other side of the membrane. Waste matter passes from the blood through the membrane because of the lower concentration of waste matter in the dialysate solution than in the blood.

In addition to the detoxication of the blood, it is necessary to withdraw excess water from the blood of the patient. Removal of water from the blood is known as ultrafiltration. Ultrafiltration is accomplished by applying a pressure difference across the membrane (transmembrane pressure) so that the blood-carrying side of the membrane has a positive pressure and the side carrying dialyzing fluid has a negative pressure or a pressure which is less positive. The rate of ultrafiltration is dependent upon the transmembrane pressure. The higher the transmembrane pressure, the greater is the removal of water from the blood.

Because of the wide difference in the ultrafiltration output among various dialyzers, it is necessary to monitor the withdrawal of fluid, e.g. by periodically weighing a patient or by using a bed scale. An uncertainty in the ultrafiltration process is the preselection of the transmembrane pressure required for obtaining the desired ultrafiltration rate. It would be better, instead of preselecting the transmembrane pressure, [i.e., in the usual practice preselecting the negative pressure of the dialysis liquid] to be able to set or indicate directly the desired ultrafiltration rate. In principle, indication of the quantity of water removed by ultrafiltration is possible by the use of precision flowmeters. However, despite extremely accurate measuring equipment, measurement is only possible within very limited accuracy because the quantity of water removed by ultrafiltration is very small in proportion to the quantity of dialysate.

A known dialysis system is disclosed in U.S. Pat. No. 3,844,940. This prior art dialysis system comprises a switching device for disconnecting the dialysate path containing one chamber of the dialyzer from the dialysate source. A controlled suction pump positioned downstream from the dialyzer maintains the transmembrane pressure constant during an interruption phase. The quantity of liquid transported out of the dialyzer substantially corresponds to the quantity of liquid removed by ultrafiltration. The liquid is conveyed into a measuring vessel which comprises a level gauge having two capacitor electrodes. In this manner, the quantity of liquid removed from the blood by ultrafiltration during the disconnection of the dialysate source from the dialysate path is measured.

The measuring phase is the phase when the rate of ultrafiltration or the quantity of liquid removed from the blood by ultrafiltration is measured. During the measuring phase, the dialysate source has been disconnected.

The operative phase is the phase when the dialysate source is connected to the dialysate path and providing dialysate solution for flow through one chamber of the dialyzer. During the operative phase, detoxification is taking place. Ultrafiltration is also taking place dependent upon the magnitude of the transmembrane pressure.

The known dialysis apparatus has the disadvantage that only the blood pressure is measured for the determination of the transmembrane pressure. This blood pressure value is compared with the pressure at the exit from the dialysate chamber and the difference is used as the transmembrane pressure. Since the dialysate does not flow through the dialyzer during the interruption phase, the flow resistance or respectively the pressure drop in the dialyzer is not taken into account. In addition, the venous blood pressure measured on the patient does not furnish a representative value for the pressure in the blood chamber of the dialyzer. During the measuring phase, therefore, pressure conditions prevail in the dialyzer which differ considerably from the pressure conditions during the operative phase. The device for measuring the transmembrane pressure regulates the suction pump during the measuring phase in a manner which does not correspond to the conditions during the operative phase. In addition, the known system involves merely a measuring system which does not indicate how the transmembrane pressure must be changed in order to obtain a desired ultrafiltration flow. Furthermore, the liquid volume measuring device, operating with two electrodes, is relatively imprecise because its result depends on the conductivity of the dialysate solution.

OBJECT OF THE INVENTION

It is therefore an object of the present invention to provide a dialysis system capable of an improved measurement of the ultrafiltration rate.

It is a further object of the present invention to provide a dialysis system which permits during the measuring phase a more precise stabilization of the transmembrane pressure at the value maintained during the operative phase thereby providing a more precise measurement of the ultrafiltration rate.

It is yet another object of the present invention to provide an improved method of operating a dialysis system for obtaining a desired ultrafiltration rate.

These and other objects will become apparent from the following description and claims in conjunction with the drawings.

SUMMARY OF THE INVENTION

For the solution of the problems associated with the prior art, the present invention provides that the liquid present in the dialysate flow path circulates in a cycle through the dialysate flow path suction pump and the dialyzer even when the dialysate source is disconnected from the dialysate flow path. The transmembrane pressure is maintained constant by regulation of the suction pump.

The dialysis system of the present invention may be generally summarized as comprising a dialyzer having two chambers separated by a membrane wherein one chamber is connected in a dialysate flow path and the other chamber is connected in a blood flow path, a suction pump disposed in the dialysate flow path for maintaining the transmembrane pressure, means for regulating said suction pump as a function of the transmembrane pressure, a dialysate source connected to the dialysate flow path, first valve means for disconnecting the dialysate flow path from the dialysate source, and volume measuring means connected via second valve means to the dialysate flow path for measuring the overflow volume of liquid present in the dialysate flow path when the dialysate source is disconnected from the dialysate flow path; the improvement comprising:

conduit means for maintaining circulation of the liquid present in the dialysate flow path in a cycle through said suction pump via said dialyzer when said dialysate source is disconnected from said dialysate flow path, and with said means for regulating said suction pump maintaining the transmembrane pressure constant by regulation of said suction pump.

BRIEF DESCRIPTION OF THE DRAWING

In the drawing forming part hereof, the single FIGURE of the drawing schematically illustrates one preferred embodiment in accordance with the present invention.

DESCRIPTION OF THE PREFERRED EMBODIMENTS

In order to afford a more complete understanding of the present invention and an appreciation of its advantages, a description of the preferred embodiments is presented below.

In the dialysis equipment according to the present invention, a continuous circulation of the dialysate through the dialysate flow path containing the dialyzer occurs during the measuring phase, that is, when the dialysate source is disconnected from the dialysate flow path. Because of this, the same pressure drop is maintained at the dialyzer as exists during the operative phase. Thus, the conditions under which the transmembrane pressure is determined in the two phases are the same. The result is that the transmembrane pressure, which is maintained constant by the regulation of the suction pump, is maintained exactly at the same value in both phases. It is of particular importance that this stabilization of the transmembrane pressure is independent of the pressure drop of the dialyzer, i.e. independent of the flow resistance of the dialyzer. This flow resistance depends on the type of dialyzer used and may be subject to differences even among units of the same model. In the dialysis system of the present invention, the transmembrane pressure is maintained very exactly constant independent of the type of dialyzer used. The quantity of ultrafiltrate can thus be measured exactly. The ultrafiltration rate measured during the measuring phase corresponds exactly to the ultrafiltration rate that prevails during the operative phase.

According to a preferred embodiment of the present invention, the dialysate path is connected via a valve device 2, 14 to a dialysate source 1 and to a drain 15. In one operating state of the valve device 2, 14, the dialysate flow path forms a cycle separated from the dialysate source 1 and from the drain 15 which cycle contains one chamber 101 of the dialyzer, the suction pump 13, and the overflow connection for the volume measuring device 5. The volume measuring device 5 comprises a vessel which receives that additional quantity of liquid which gets into the cycle during the measuring phase as a result of ultrafiltration. This additional quantity of liquid corresponds to the volume of ultrafiltrate. The volume measuring device operates, for example, with an ultrasonic level meter, or photoelectric cells on different levels, or the like, in order to measure the overflow quantity of liquid displaced from the cycle with high accuracy.

In flow direction upstream from the dialyzer, a volumetric feed pump 6 is preferably connected into the dialysate flow path. This feed pump 6 serves to maintain the liquid flow. The suction pump 13 is regulated in such a way that it creates in the dialysate chamber 101 of the dialyzer disposed between these two pumps a negative pressure relative to the pressure prevailing in the blood chamber 102 of the dialyzer.

An exact measurement of the transmembrane pressure is made possible by the fact that a pressure measuring device is connected to each of the inlets and outlets of the two chambers of the dialyzer. The transmembrane pressure is determined by averaging the two pressure values on each side of the membrane 103 and by subtraction of the average pressure values. Such a measuring method permits determining a "middle transmembrane pressure," that is, the pressure difference assumed at the center of the membrane of the dialyzer. This takes into consideration the pressure drops which result in both chambers of the dialyzer due to the flow resistances of the chambers.

The volume measuring device has an overflow connectable to the inlet side of the suction pump 13 via a valve 16. In this way disinfection and flushing are made possible.

For the dialysis equipment of the invention, a preferred method of operation is provided wherein the transmembrane pressure TMP 2 needed to be set in order to obtain a desired ultrafiltration rate is determined according to the equation:

$$TMP\ 2 = \frac{t_1 \times TMP\ 1}{t_2}$$

TMP 1 is the preset transmembrane pressure. Time $t_1$ is the time required for filling a predetermined volume V of the volume measuring device with liquid at this transmembrane pressure TMP 1. Time $t_2$ is the time required for filling the predetermined volume V at the desired ultrafiltrate flow.

Within the scope of the above described measuring method, it is basically possible to measure volume instead of the time. According to an alternate method of operation in accordance with the present invention, the transmembrane pressure TMP 2 needed to be set in order to obtain a desired ultrafiltration flow rate is determined according to the equation:

$$TMP\ 2 = V_2/V_1 \times TMP\ 1.$$

$V_1$ is the volume of liquid overflowing from the closed cycle during a given measuring time at the previously prevailing transmembrane pressure TMP 1. $V_2$ the volume of liquid overflowing during the same measuring time at the desired ultrafiltrate flow.

With reference to the single FIGURE of the drawing, an embodiment of the present invention is explained more specifically.

The schematically shown dialyzer 10 has two chambers 101, 102 separated by a membrane 103. Chamber 101 is the dialysate chamber and chamber 102 is the blood chamber. In a practical form of realization, the dialyzer 10 may comprise hollow fiber bundles. The blood is passed through the hollow fibers whereas the dialysate flows around the hollow fibers. Hollow fiber dialyzers are already known in the art.

Assume that the dialysate liquid stream flows through the chamber 101 at a rate of 500 ml/min. To this dialysate liquid stream is added an ultrafiltration stream removed from the blood of the patient. This ultrafiltration stream may be, e.g. 5 ml/min, and must be determined with an accuracy of better than 2%. To achieve this, the consumed dialyzing liquid stream leaving chamber 101 must be measured with a maximum error of 0.2 per thousand. There is thus an extremely high accuracy requirement.

Volumetric feed pump 6 is connected in fluid communication by conduit means to the dialysate source 1 via a switching valve 2 and a throttle point 3. The feed pump 6 is connected in fluid communication by conduit means via the switching valve 7 with the inlet 101a of chamber 101 of dialyzer 10. The outlet 101b of chamber 101 is connectd in fluid communication to the inlet of suction pump 13. The outlet of suction pump 13 is connected in fluid communication via a switching valve 14 to the drain 15.

When the switching valves 2, 7 and 14 are all in their $\frac{1}{2}$ position, dialysate is supplied from dialysate source 1 via feed pump 6 to the dialyzer 10 and passes thence via suction pump 13 to drain 15. Valves 2, 7 and 14 can be switched between the $\frac{1}{2}$ and $\frac{1}{3}$ positions. Valves 2 and 14 are coupled together and form the valve device 2, 14. In the $\frac{1}{3}$ position of this valve switching device 2. 14, the dialysate source 1 is connected directly with drain 15, whereas the outlet of suction pump 13 is connected to the inlet of the volumetric feed pump 6.

At each of the inlets and outlets of the two chambers 101 and 102, a pressure gauge 8, 9, 11, 12 is connected. The pressure gauges 8 and 12 at the inlet 101a and outlet 101b of the dialysate chamber 101 furnish the pressure values A and b. An electrical signal representative of the pressure values A and B are inputted into a computer circuit 17. In the computer circuit 17 the mean value $$\frac{A+B}{2} = C$$

of the pressure values A and B is formed. Similarly, the output signals of the pressure gauges 9 and 11, which are connected at the inlet and outlet of blood chamber 102, furnish pressure values E and D. These pressure value signals are inputted into a computer circuit 18, which forms the mean $$\frac{D+E}{2} = F$$

of the two pressure values D and E. The output signals of the computer circuits 17 and 18 representing C and F are inputted to a subtraction circuit 19 which forms from the output signals C and F the difference $F-C$. The output signal of the subtraction circuit 19 represents the measured mean transmembrane pressure TMP. The measured transmembrane pressure TMP signal is inputted into a comparator circuit 20. A preset desired transmembrane pressure $TMP_s$ signal is also inputted into comparator circuit 20. In the comparator circuit 20, the measured value TMP is compared with the preset desired mean transmembrane pressure value $TMP_s$ and the difference between the two values is supplied as an output signal from comparator 20 which is used for the regulation of the suction pump 13. In this way, the suction pump 13 always develops a suction force such that the mean transmembrane pressure TMP in the dialyzer 10 is maintained at the desired mean transmembrane pressure value $TMP_s$.

The inlet side of the feed pump 6 is connected in fluid communication via a valve 4 with the lower end of an upright measuring vessel 5. The upper end of the measuring vessel 5 is connected in fluid communication via a switching valve 16 in the $\frac{1}{2}$ position to the atmosphere for deaeration with the atmosphere. With switching valve 16 in the $\frac{1}{3}$ position, measuring vessel 5 is in fluid communication with the inlet to the suction pump 13.

In the operative phase, the feed pump 6 creates a dialysate flow from the dialysate source 1 via the switching valve 2, throttle 3 and switching valve 7 through the dialyzer 10. The regulated suction pump 13 creates in chamber 101 the negative pressure relative to blood chamber 102 required to obtain the desired preset transmembrane pressure. The dialysate combines with the ultrafiltration component in chamber 101 and then flows off to drain 15 via the switching valve 14. Shortly after reaching the first adjusted desired value $TMP_s$ of the transmembrane pressure, the switching valves 2 and 14 switch to the paths $\frac{1}{3}$. At the same time, valve 4 opens. When this is accomplished, the measuring phase begins. By means of the feed pump 6, the dialysate remaining in the uncoupled cycle of the dialysate flow path recirculates in this cycle which has been uncoupled from the dialysate source 1 and from drain 15. Since the liquid volume increases because of the continuing ultrafiltration, the dialysate rises over valve 4 into the measuring vessel 5. There is a level gauge in the measuring vessel. The rate of rise of the liquid in the measuring vessel gives a measurement of the quantity of the ultrafiltrate obtained. With this result obtained, the necessary mean transmembrane pressure for attaining a preselected ultrafiltration rate can be calculated according to the following algorithm:

Let:
V be a selected volume of the measuring chamber;
$Q_{UF}$, the desired ultrafiltration rate;
$t_2$, the time needed to fill up the volume V at the rate $Q_{UF}$;
TMP 1, the initially set transmembrane pressure;
$t_1$, the measured time required on the basis of the value TMP 1 to fill up the volume V;
TMP 2, the transmembrane pressure which must be set to obtain the ultrafiltration rate $Q_{UF}$.

From this we obtain:

$$t_2 = V/Q_{UF}$$

$$TMP\,2 = \frac{t_1 \times TMP\,1}{t_2}$$

After completion of measuring and calculation, the measuring device switches the switching valves 2 and 14 back to the paths ½ so that the operative phase begins again. Due to the light negative pressure created between the throttle 3 and feed pump 6, the measuring vessel 5 is evacuated until the zero level is reached. After the zero level has been reached, valve 4 is closed again.

As the ultrafiltration factor of the dialyzer 10 may vary during the dialysis, it is necessary to determine the ultrafiltration rate of the dialyzer anew at regular intervals. For this purpose, the measurement is repeated at preselected intervals.

In principle, the measurement described above with reference to a time measurement can also be carried out as a volume measurement. If:

$V_1$ is the volume reached in the measuring vessel at the value TMP 1;

$V_2$ is the volume reached in the measuring vessel at the desired ultrafiltration rate $Q_{UF}$; and $t_3$ is a constant measuring time; then:

$$V_2 = Q_{UF} \times t_3$$

$$TMP\,2 = V_2/V_1 \times TMP\,1.$$

After termination of the dialysis, it is necessary to disinfect the entire system and thereafter to flush it. For this purpose, the switching valve 16 is switched from the ½ position to the ⅓ position and valve 4 is opened. At the same time, the feed pump 6 is adjusted to one half of its normal speed so that a partial stream of the disinfection solution flows via the short-circuited connections 101a and 101b of dialyzer 10 and the other partial stream via the measuring vessel 5.

After a sufficient flushing time, the disinfection is stopped.

Some patients are treated with what is called a sequential therapy. This means that first an ultrafiltration is carried out without dialysate flow, and after sufficient removal of water from the patient, one switches to dialysis with simultaneously reduced or suppressed ultrafiltration. For this purpose, valve 7 is provided, to enable the cut off of the dialysate inflow to dialyzer 10.

The computer circuits, the instrumentation and the controls have not been described herein in detail as they are conventional and may be readily supplied by one skilled in the art. Such details are unnecessary for one skilled in the art to understand and practice the disclosed invention.

Although preferred embodiments of the present invention have been described in detail, it is contemplated that modifications may be made within the spirit and the scope of the invention.

What is claimed is:

1. A dialysis system comprising:
   a dialyzer having two chambers separated by a membrane wherein one chamber is a dialysate chamber connected in a dialysate flow path, said dialysate flow path comprising an upstream portion and a downstream portion, and the other chamber is a blood chamber connected in a blood flow path;
   said dialysate chamber having an inlet connected to the upstream portion of said dialysate flow path and an outlet connected to the downstream portion of said dialysate flow path;
   a volumetric feed pump located in the upstream portion of said dialysate flow path to feed liquid present in said dialysate flow path to the inlet of said dialysate chamber;
   one suction pump located in the downstream portion of said dialysate flow path to draw on the outlet of said dialysate chamber for maintaining transmembrane pressure in said dialyzer;
   a dialysate reservoir connected in fluid communication with the upstream portion of said dialysate flow path at a location upstream from said volumetric feed pump;
   a dialysate drain connected in fluid communication with the downstream portion of said dialysate flow path at a location downstream from said one suction pump;
   first valve means for selectively disconnecting said dialysate reservoir and said dialysate drain from said dialysate flow path thereby providing a measuring phase and for selectively connecting said dialysate reservoir and said dialysate drain to said dialysate flow path thereby providing an operating phase;
   volume measuring means comprising a measuring container connected to said dialysate flow path via second valve means for measuring the overflow of liquid present in said dialysate flow path when said dialysate reservoir and said dialysate drain are disconnected from said dialysate flow path during said measuring phase to determine a preselected transmembrane pressure;
   means for permitting said measuring container to communicate with atmosphere when said dialysate reservoir and said dialysate drain are disconnected from said dialysate flow path during said measuring phase;
   means responsive to transmembrane pressure for regulating said suction pump to maintain said preselected transmembrane pressure when said dialysate reservoir and said drain are connected to said dialysate flow path during said operating phase; whereby
   said volumetric feed pump feeds liquid present in said dialysate flow path to the inlet of said dialysate chamber both when said dialysate reservoir and said dialysate drain are connected and disconnected from said dialysate flow path during said operating phase and said measuring phase respectively; and
   said one suction pump maintains said transmembrane pressure both when said dialysate reservoir and said dialysate drain are connected and disconnected from said dialysate flow path during said operating phase and said measuring phase respectively.

2. A dialysis system as recited in claim 1 wherein said other chamber has an inlet and an outlet;
   a first pressure gauge is connected to said one chamber inlet for measuring a first pressure;
   a second pressure gauge is connected to said one chamber outlet for measuring a second pressure;
   a third pressure gauge is connected to said other chamber inlet for measuring a third pressure;
   a fourth pressure gauge is connected to said other chamber outlet for measuring a fourth pressure;

means for determining the average of said first and second pressures wherein said average represents the average pressure in said one chamber;

means for determining the average of said third and fourth pressures wherein said average represents the average pressure in said other chamber;

means for subtracting the average of said first and second pressures from the average of said third and fourth pressures wherein said subtraction represents the transmembrane pressure.

3. A dialysis system as recited in claim 1 having an overflow conduit means connecting said volume measuring means to the inlet side of said suction pump and third valve means disposed in said overflow conduit means.

4. A dialysis system as recited in claim 1 having a throttle device positioned in said dialysate flow path between the connection of said volume measuring means and the connection of said dialysate source to said dialysate flow path.

5. A method for setting the transmembrane pressure in the dialysis system according to claim 1 for obtaining a desired ultrafiltrate flow, said method comprising:

disconnecting said dialysate source from said dialysate flow path;

maintaining circulation of liquid present in said dialysate flow path within said dialysate flow path after said disconnecting step;

determining the previously set transmembrane pressure TMP 1 by measuring the pressure of liquid flowing in said one chamber and measuring the pressure of blood flowing in said other chamber;

measuring the time $t_1$ required to fill a predetermined volume V of said volume measuring means at said previously set transmembrane pressure TMP 1;

determining the time $t_2$ required to fill said predetermined volume V at said desired ultrafiltrate flow;

calculating the transmembrane pressure TMP 2 required to provided said desired ultrafiltrate flow by the equation:

$$TMP\ 2 = \frac{t_1 \times TMP\ 1}{t_2}$$

regulating said suction pump to obtain said transmembrane pressure TMP 2.

6. A method for setting the transmembrane pressure in the dialysis system according to claim 1 for obtaining a desired ultrafiltrate flow, said method comprising:

disconnecting said dialysate source from said dialysate flow path;

maintaining circulation of liquid present in said dialysis flow path within said dialysate flow path after said disconnecting step;

determining the previously set transmembrane pressure TMP 1 by measuring the pressure of liquid flowing in said one chamber and the pressure of blood flowing in said other chamber;

measuring the volume $V_1$ of liquid overflowing into said volume measuring means during a selected time interval at said previously set transmembrane pressure TMP 1;

determining the volume $V_2$ of liquid that would flow into said volume measuring means during said selected time interval at said desired ultrafiltrate flow;

calculating the transmembrane pressure TMP 2 required to provide said desired ultrafiltrate flow by the equation:

$$TMP\ 2 = V_2/V_1 \times TMP\ 1$$

regulating said suction pump to obtain said transmembrane pressure TMP 2.

* * * * *

UNITED STATES PATENT AND TRADEMARK OFFICE
CERTIFICATE OF CORRECTION

PATENT NO. : 4,735,727
DATED : April 5, 1988
INVENTOR(S) : R. Heitmeier et al.

It is certified that error appears in the above-identified patent and that said Letters Patent is hereby corrected as shown below:

At Col. 5, Line 33, delete "connectd" and insert -- connected --

At Col. 5, line 43, delete "12.14" and insert -- 12, 14 --.

At Col. 5, line 51, delete "b" and insert -- B --.

At Col. 10, line 16, delete "sis" and insert -- sate --.

Signed and Sealed this

Twenty-seventh Day of December, 1988

Attest:

DONALD J. QUIGG

*Attesting Officer*     *Commissioner of Patents and Trademarks*